United States Patent [19]
Frush

[11] Patent Number: 5,244,388
[45] Date of Patent: Sep. 14, 1993

[54] DENTAL APPLICATOR

[76] Inventor: John P. Frush, 965 Rancho Alisal Dr., Solvang, Calif. 93463

[21] Appl. No.: 792,489

[22] Filed: Nov. 15, 1991

[51] Int. Cl.$^5$ ............................................... A61C 5/04
[52] U.S. Cl. ..................... 433/90; 433/214; 222/575
[58] Field of Search ............ 433/90, 89, 40, 214; 222/490, 566, 575

[56] References Cited

U.S. PATENT DOCUMENTS

| | | | |
|---|---|---|---|
| 3,304,608 | 2/1967 | Frohnecke | 433/40 |
| 3,436,828 | 4/1969 | Dragan | 433/90 |
| 3,618,216 | 11/1971 | Jaeger | 433/90 |
| 4,255,140 | 3/1981 | Marshall | 433/90 |
| 4,483,675 | 11/1984 | Marshall | 433/40 |
| 4,619,613 | 10/1986 | Dragan | 433/90 |
| 4,682,950 | 7/1987 | Dragan | 433/90 |

Primary Examiner—John J. Wilson
Attorney, Agent, or Firm—Marvin E. Jacobs

[57] ABSTRACT

Dental impression material is applied to the surfaces of teeth under pressure and in a direction of flow perpendicular to the underlying tooth surface. The impression material is pushed into the sulci, interstices of teeth and crevices in adjacent tissues which presses air out and prevents formation of voids. The applicator can be an accessory which is frictionally and sealingly received over the tip of a syringe. The distal end of the applicator may contain a vertical flap spaced from the outlet orifice and adjacent side walls, forming a chamber. As the impression material is extruded, it collects in the chamber under pressure. The end wall may be hinged to wipe the material onto surfaces and may be cut into miniflaps to conform to cusps and adjacent depressions on occlusal surfaces of teeth.

18 Claims, 4 Drawing Sheets

DENTAL APPLICATOR

CROSS-REFERENCE TO DISCLOSURE DOCUMENT

The present invention was disclosed in Disclosure Document No. 262901, filed Sep. 17, 1990. Please retain the Disclosure Document.

TECHNICAL FIELD

The present invention relates to a device which is utilized to form dental impressions and, more particularly, this invention relates to an applicator for accurately applying dental impression material to the surfaces of teeth and adjacent tissues in a fully or partially dentulous mouth.

BACKGROUND OF THE INVENTION

A dental appliance is made on an artificial stone cast of the mouth. A primary impression must be made of the mouth in order to produce the artificial stone cast. The technical quality of a dental appliance is in direct proportion to the accuracy of the primary impression, the correct clinical procedure and the accurate coverage of the teeth and pertinent soft tissues with the impression material.

Present techniques for forming dental impressions in fully or partially dentulous mouths are generally divided into two categories: The first is a "primary" impression and employs a stock dental tray filled with soft impression material, usually a dental alginate. The soft material is carried into the patient's mouth by the impression tray. When positioned or centered over the teeth and other areas of interest, the soft material is pushed over the dental structures by the application of vertical pressure on the tray. This carries the soft material over the teeth and related tissues in the dental arch. The impression material sets in a few minutes after mixing and is transformed into a flexible, solid mass which no longer flows. The flexibility of the impression material allows its removal from the undercuts formed by the bulging surfaces of the teeth and related tissues.

This "primary" impression is used to form a cast of artificial stone, which is a positive reproduction of the dental arch and oral tissues recorded in this "primary" impression. The disadvantages of using a case made from the "primary" impression as a final working cast are: (1) insufficient coverage of the edentulous areas and faulty peripheral extensions of the dental arch; and (2), lack of perfect detail caused by failure of the impression material to reach every portion of the teeth, the gingival crevices and the occlusal sulci. This failure is caused by the entrapment of air as the impression material, being applied without sufficient pressure and proper direction of flow, is not forced into the deeper crevices and depressions.

This requires the implementation of a "secondary" impression which employs the use of a custom dental tray formed on the primary cast. A custom tray is made of hard material and is formed loosely to fit the teeth and tissues and is supposed to provide the necessary coverage of teeth and soft tissues, as well as establishing the proper extensions of the peripheral borders. The construction of a custom tray is a separate procedure accomplished between the first and second operative appointments. The patient must return a second time to the dental office so that another impression can be made, using the custom tray, for the final working cast on which the appliance is constructed. When employing a custom tray, a soft impression material is also used in the same manner as with the "primary" impression. However, a "secondary" impression of the mouth with a custom tray does not thoroughly correct the main disadvantage associated with the "primary" impression, i.e., air entrapment. The soft impression material which flows around the teeth and the soft tissues of the impression area, in either the "primary" or "secondary" impression, traps air in many of the critical areas of the impression. When the material sets and the impression is removed from the mouth, air voids appear on the surface of the impression. When the impression is poured with dental stone, these air voids in the impression show up on the final cast as stone bubbles and other imperfections. These must be mechanically carved away with a sharp instrument from critical surfaces before a dental appliance can be constructed. However, this often leaves an imperfect cast, and many times the correction is not possible, such as in an occlusal rest groove prepared by the operator. If the mechanical correction of these critical areas with a sharp instrument is not perfect, the appliance will not fit the teeth and will require additional time-consuming adjustments by the operator who tries to make it useful.

Some dentists attempt to prevent air voids in the impression by applying dabs of the impression material to the teeth with their index finger. Another method is to apply the impression material to the teeth with a syringe. Both of these procedures produce an imperfect application of the impression material and consumer critical time. This often results in the materials setting into its elastic form before the impression tray and the impression material can be inserted into the mouth and over the teeth, thus requiring a new impression. Also, these methods do not totally alleviate the problem of imperfections in the cast caused by air voids. An impression free of air voids is needed to provide an accurate cast for the construction of a removable appliance which will be comfortable to the patient without the necessity of mechanically correcting the cast and grinding the insides of the metal clasps in order to make the appliance fit.

SUMMARY OF THE INVENTION

This invention is based on the recognition that prior-art applications of impression material on and around the teeth are unable to obtain accurate impressions because they fail to apply the impression material in a way that displaces the air on the surfaces of the teeth, in the gingival crevices and inter-dental interstices. In the invention, the impression material is applied to all the teeth and immediate supporting structures under pressure and in a direction of flow perpendicular to the underlying tooth surface which pushes the air out of the sulci, the interstices and crevices where it traditionally is trapped and otherwise would form a void in the impression material.

These and other features and many other attendant advantages of the invention will become apparent as the invention becomes better understood by reference to the following detailed description, when considered in conjunction with the accompanying drawings.

DETAILED DESCRIPTION OF THE INVENTION

Figures 1, 1A, 1B, 1C:
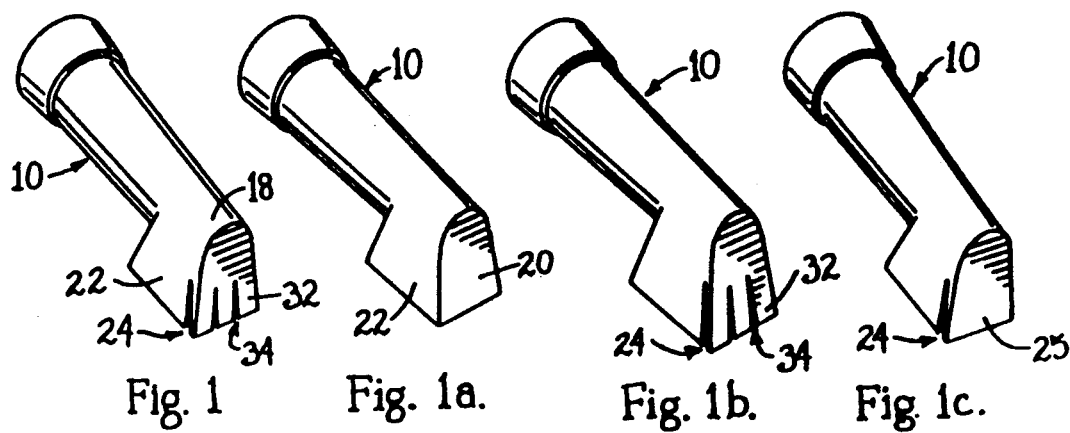
FIGS. 1, 1A, 1B and 1C are perspective views of dental impression applicator devices according to the invention.
Figure 2:
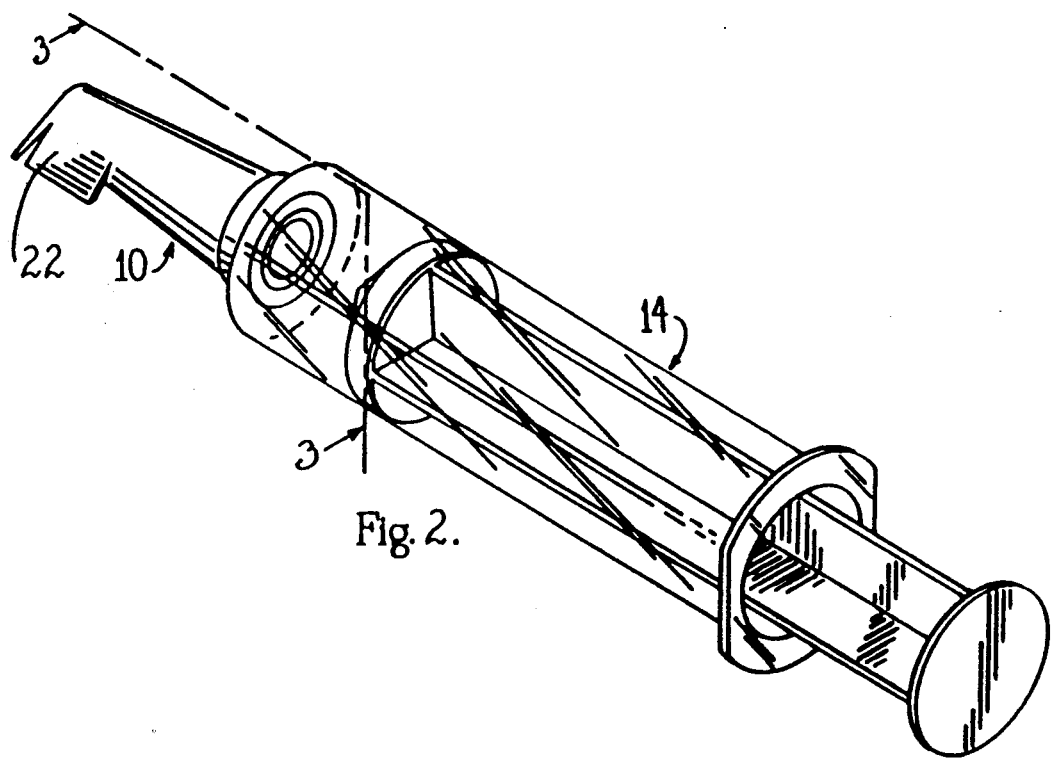
FIG. 2 is a perspective view of an applicator device assembled with a dental impression syringe.
Figure 3A:
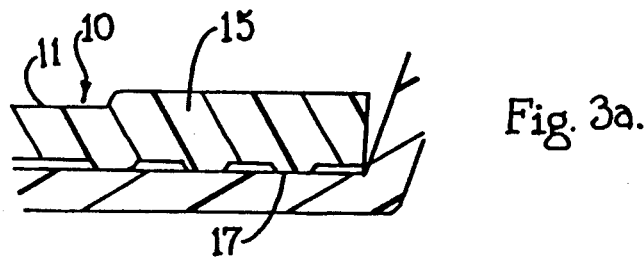
FIG. 3A is an enlarged view in section of the detail circled in FIG. 3.
Figure 3:
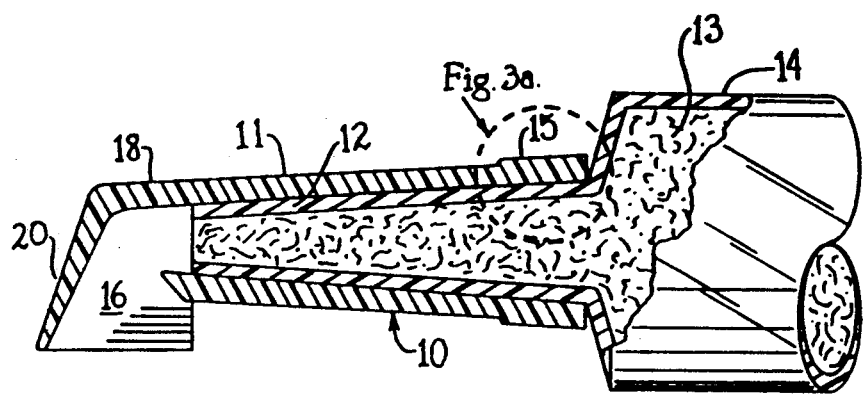
FIG. 3 is a view in section taken along Line 3—3 of FIG. 2.

Referring now to FIGS. 1-3, the applicator device 10 of this invention is an accessory which is attached to the tip 12 of a syringe 14 containing impression material 13. As shown in FIG. 3A, the applicator 10 has a sleeve 11 which is sealingly received on the tip 12 of the syringe 14. The sleeve has a thickened end forming a collar 15 having internal rings 17 for maintaining frictional engagement with the tip 12. The applicator 10 has a chamber 16 which receives the impression material under pressure from the syringe 14. As seen in FIG. 3, the chamber 16 is formed of a top wall 18, distal wall 20 and side walls 22, with no mesial wall. The applicator 10 is preferably made of flexible material which adapts to the exposed surfaces of the teeth when the chamber 16 is pressed vertically over the body of the teeth from the direction of the chewing surface. The syringe 14 holds the impression material 13, which in turn is expelled into the chamber of the applicator.

Figure 4:
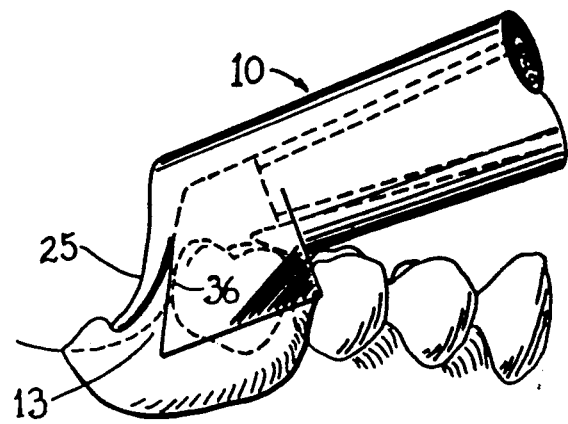
FIG. 4 is a side view showing application of dental impression material to the last tooth in the dental arch.

As shown in FIG. 1A, the distal or end wall 20 can be attached to the outer side walls 22, or as shown in FIGS. 1B and 1C, the distal or end wall 20 is detached from the outer side walls 22 at the corners 24, in such a way as to form a separate, flexible, vertical flap 25 which can move to a horizontal position independently of the side walls 22. As shown in FIG. 4, in its normal vertical position, the end wall 20 places and holds the stream of impression material being dispensed from the chamber, under pressure, against the distal surface 36 of a tooth, which surface has been exposed by the extraction of an adjacent tooth, or is the last tooth in the dental arch. The end wall flap 20 directs a stream 29 of impression material vertically along the entire length of the tooth's exposed distal surface 36, eliminating air voids by virtue of the uni-directional movement of the impression material, which is controlled by the pressure flap 20 against the distal surface of the tooth. This prevents the casual escape of the material away from the tooth's surface, a common occurrence which would produce an air void and result in an inaccurate impression of the distal tooth surface and its gingival crevice.

Figure 5:
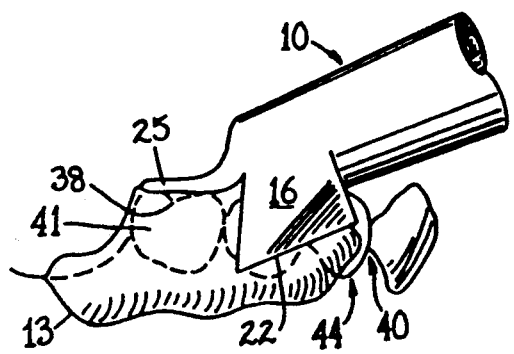
FIG. 5 is a side view showing the application of impression material to the occlusal surfaces of teeth.

Another advantage of this flexible wall 20, as shown in FIG. 5, is that of a pressure flap 25 in its horizontal position, which, in concert with the inner and outer flexible walls 22, simultaneously compresses the flow of impression material against the contiguous occlusal surfaces 38 of the posterior teeth 41, the inner (lingual) and outer (buccal) surfaces 38, the interstices 40 between the teeth and the gingival crevices 44 around these teeth. As the chamber 16 is pressed vertically over the posterior teeth, the distal wall 20 is deflected to its horizontal position by the occlusal surfaces of the teeth. The inner and outer side walls 22 now cover the sides of the teeth, and compress the impression material against the buccal 42 and lingual tooth surfaces and into their interstices 40. The distal flap 25, now in a horizontal position, compresses the material against the occlusal surfaces 38 of the teeth, and, by virtue of the missing mesial wall of the chamber, forces the impression material to flow ahead of the flap as the pressure chamber is moved mesially forward on the occlusal surfaces of the teeth. In this deflected, horizontal position, the flap 25 directs the flow of the impression material against the occlusal surfaces under pressure. However, the flap 25 can only lie on the highest contours (cusps) of the teeth and cannot conform to the uneven occlusal surfaces of the teeth with their peaks and valleys, known as cusps and sulci, allowing possible entrapment of air in the deepest sulci and occlusal-rest preparations.

Figure 6:
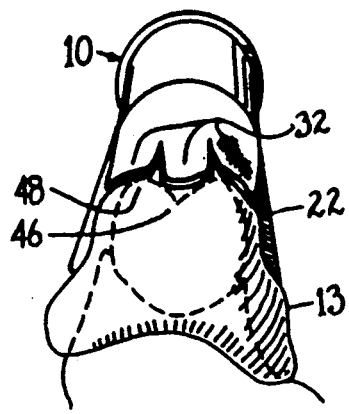
FIG. 6 is an end view showing application of impression material to the occlusal cusps and valleys of teeth.

For this reason, as shown in FIGS. 1 and 1b, the distal flap 25 can be divided into several mini-flaps 32 by dividing the flap with vertical cuts 34. In this way, the end wall forms a continuous surface when the wall is in its vertical position, but the mini-flaps function independently when in a horizontal position, as illustrated in FIG. 6. These mini-flaps 32 enter and force the impression material into the occlusal valleys 46 and around the peaks 48 of the cusps, preventing entrapment of air as the chamber, now encompassing the three (3) surfaces of the posterior teeth, is moved from the distal limits of the residual dental arch forward in a single motion.

The flow of impression material to the surfaces of the teeth is kept constant and in sufficient volume to maintain a positive pressure in the chamber. This forces the material into the deepest crevices and occlusal sulci as the chamber is moved from the distal-most teeth of the arch forward to the mid-line for an impression free of air voids.

Figure 7:
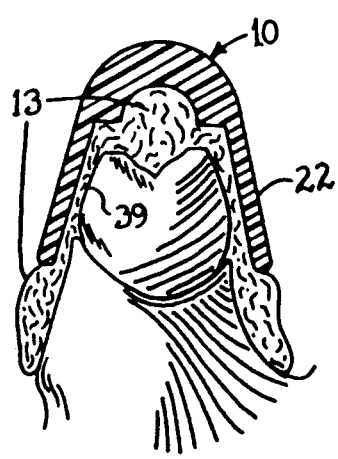
FIG. 7 is a schematic view showing the flow of impression material and air from the chamber into the vestibules.

The advantages of this invention over prior art devices and methods is an accurate and fast adaptation of an impression material to the teeth. The application of impression material under confined pressure results in an air-displacing direction of flow, as shown in FIG. 7. As the impression material flows down the buccal and lingual sides of the teeth, it carries entrapped air with it. The air is released as it is carried past the side walls 22 into the vestibules 31. Furthermore, the mechanical adaptation of the impression material into the occlusal sulci by the action of the mini-flaps assures the removal of air bubbles. The applicator described in this invention is used before the filled impression tray is carried into the mouth.

The applicator of this invention can be utilized to form an impression of a single tooth. In this case, the end wall 20 need not be hinged or cut at its edges, as shown in FIG. 1A, since the applicator is not swept over the occlusal surface of adjacent teeth. The chamber 16 may also contain a long front wall 41 facing the end wall, as shown in FIG. 1B. The chamber may also be cylindrical in shape, with mini-flaps being formed around the entire circumference of the cylinder.

Figure 8A:
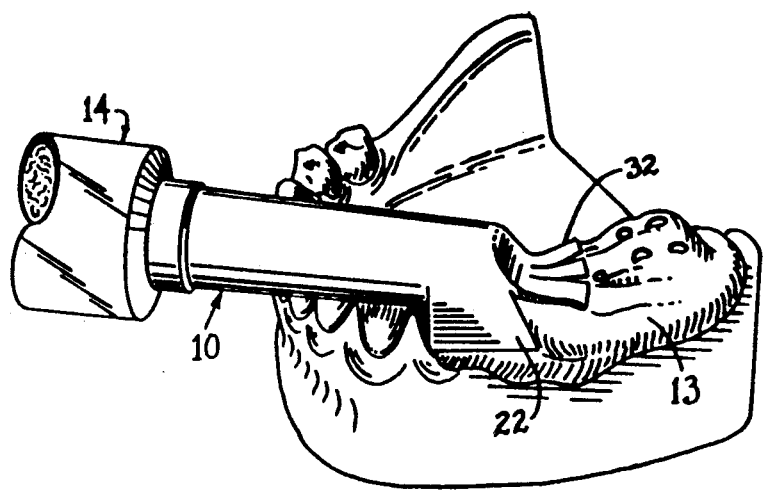
FIGS. 8A and 8B are schematic views showing the 90 degree turn of the applicator from the occlusal to the buccal surface of teeth.
Figure 8B:
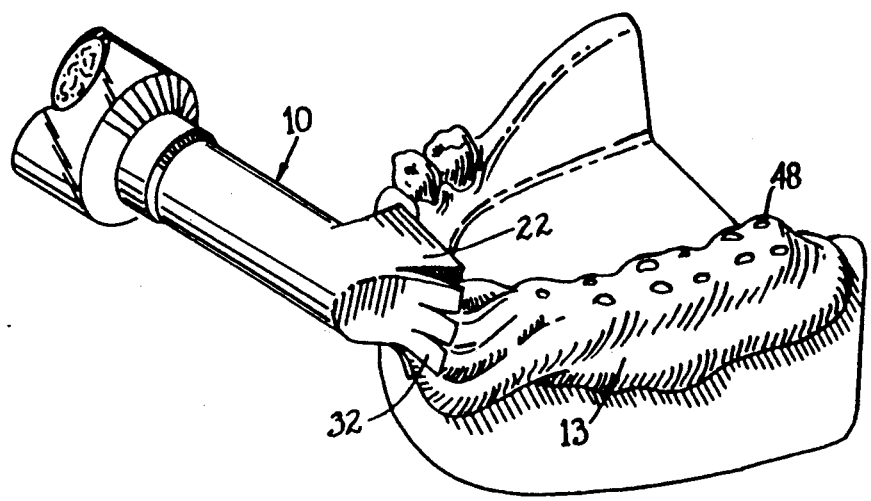

The applicator can be used to apply the impression material to the labial and lingual tooth surfaces of the anterior teeth by turning the applicator 90 degrees from its occlusal position at the cuspid tooth, and sweeping the material onto the face and lingual surface of these teeth with the compressive action of the mini-flaps, as shown in FIGS. 8A and 8B. It is important to make an accurate impression of the buccal and labial vestibules for accurate border extensions of the appliance in situations where this is indicated. Proper extension is related to a "border molded" impression of the vestibules providing a cast of these areas to which a denture or partial denture border is extended for comfort, cleanliness, and retention.

Such a "border molded" impression of these areas, to be useful, must be free of air voids. To be free of air voids, impression material must completely fill the vestibules. This cannot always be accomplished by the impression material in the impression tray, as the tray is inserted into the mouth and over the teeth after the application of the syringe material. In fact, without the vestibules being filled first with the syringe material, air voids are almost a certainty in the vestibules. In a variation of this invention, by lengthening the side walls of the chamber, the impression material may be directed to the labial and buccal vestibules for an impression of these difficult structures, free of air voids, simultaneously with the application of the impression material to the teeth and their supporting structures.

It is to be realized that only preferred embodiments of this invention have been described, and that numerous substitutions, modifications, alterations and applications are permissible without departing from the spirit and scope of the invention as defined in the following claims.

I claim:

1. An applicator for applying dental impression material to teeth and surrounding structures which is adapted to be received on the tip of a syringe comprising in combination:
    an annular body having an axis, a proximal end, a distal end, and having an open channel joining said ends;
    the proximal end, disposed on the axis, being open and being sized to sealingly and frictionally engage the tip of said syringe;
    an opening being provided in said body adjacent the distal end of said body; and
    an end wall connected to said body at said distal end spaced from and facing said opening, a set of side walls each connected to the end wall and to the body adjacent the distal end, said side walls and end walls forming a chamber receiving the dental impression material from the opening, whereby material dispensed from said opening is directed against said end wall and is dispenses normal to the axis of the body;
    the junctures of the side walls and end walls are not connected such that the end wall is connected to the body by a live hinge; and
    said end wall having a depth greater than that of the body.

2. An applicator according to claim 1 in which the side walls are of the same length as the end wall.

3. An applicator according to claim 1 in which the end wall contains at least one slit such that it is divided into a plurality of flaps.

4. An applicator according to claim 3 in which the body and channel having a conical shape conforming to the shape of the tip of the syringe.

5. An applicator according to claim 4 in which the distal end of the applicator contains an enlarged reinforcement collar.

6. An applicator according to claim 5 in which the inner surface of the collar contains a plurality of ridges for frictionally engaging and sealing to the surface of the tip of the syringe.

7. An applicator according to claim 1 for applying dental impression material to teeth and surrounding structures which is adapted to be received on the tip of a syringe, said applicator being formed of flexible material and comprising in combination:
    an annular body having an axis proximal end, a distal end, and having an open channel joining said ends;
    the proximal end, disposed on the axis being open and being sized to sealingly and frictionally engage the tip of said syringe;
    an opening being provided in said body adjacent the distal end of said body; and
    an end wall connected to said body at said distal end spaced from and facing said opening whereby material dispensed from said opening is directed against said end wall and is dispersed normal to the axis of the body.

8. An applicator according to claim 7 in which the material is a synthetic elastomer.

9. An applicator according to claim 8 in which the material is a silicone polymer.

10. A dental impression assembly comprising in combination:
    a dental impression syringe having a tip connected to a barrel; and
    an applicator formed of synthetic elastomer for applying dental impression material to teeth and surrounding structures sealingly and frictionally received on said tip, said applicator comprising;
    an annular body having an axis proximal end, a distal end, and having an open channel joining said ends;
    the proximal end, disposed on the axis being open and being sized to sealingly and frictionally engage the tip of said syringe;
    an opening being provided in said body adjacent the distal end of said body; and
    an end wall connected to said body at said distal end spaced from and facing said opening whereby material dispensed from said opening is directed against said end wall and is dispersed normal to the axis of the body.

11. A method of applying a dental impression material to teeth and adjacent tissue comprising the steps of:
    pressurizing a column of dental impression material along the axis of the column and extruding the material through an orifice into a chamber having a top wall, side walls and an end wall facing said orifice;
    placing the chamber filled with said material onto a tooth under pressure;
    forming an impression of said tooth in said material; and
    translating said chamber across the surfaces of plurality of adjacent teeth while extruding said material through said orifice into said chamber and onto surfaces of said teeth.

12. A method according to claim 11 in which a portion of the end wall is hinged and acts to wipe the material onto the surfaces of the teeth and adjacent tissue.

13. A method according to claim 12 in which the chamber is translated over the occlusal surfaces of at least one tooth with the top wall of the cavity disposed parallel to the occlusal surface.

14. A method according to claim 13 in which the cavity is translated across the labial or lingual surfaces of adjacent teeth with the top wall of the cavity parallel to said labial or lingual surface.

15. A method according to claim 14 in which said walls are formed of flexible material and said hinged end wall is formed by partial separations provided in the lower portion of the intersections of the end wall with the side walls.

16. A method according to claim 15 in which the end wall is provided with a plurality of flaps by providing at least one slit in the lower portion of the end wall whereby adjacent variations in elevation of said tooth surfaces are simultaneously covered with impression material by the ability of the adjacent flaps to independently conform to the underlying tooth structure.

17. A method of removing air bubbles in a layer of impression material being applied to the surface of teeth and adjacent tissue comprising the steps of:
  applying the material to said surface under pressure perpendicular to said surface to form a layer;
  placing the tooth inside a chamber into which the material is extruded under pressure, and said material entraps air bubbles;
  pressing the material into crevices in the tooth surfaces by forcing a flexible flap across the layer under pressure to remove air bubbles from the layer.

18. A method according to claim 17 in which the flap is divided into separate flexible members by slits formed in the flap.

* * * * *